(12) United States Patent
Marzban et al.

(10) Patent No.: US 6,221,170 B1
(45) Date of Patent: Apr. 24, 2001

(54) MAGNETIC APPARATUS AND METHOD FOR WIPING FOG IN A DIVING MASK

(76) Inventors: Caren Marzban; Haejung Paik, both of 1130 Robinhood La., Norman, OK (US) 73072

( * ) Notice: Subject to any disclaimer, the term of this patent is extended or adjusted under 35 U.S.C. 154(b) by 0 days.

(21) Appl. No.: 09/453,180

(22) Filed: Dec. 2, 1999

(51) Int. Cl.[7] .................................................. B08B 1/00
(52) U.S. Cl. .................. 134/6; 15/220.2; 134/8; 134/22.1; 134/22.19; 134/42; 2/435; 2/438; 351/43
(58) Field of Search ............................ 15/220.2; 134/6, 134/8, 22.1, 42, 22.19; 2/435, 438; 351/43

(56) References Cited

U.S. PATENT DOCUMENTS

| | | | |
|---|---|---|---|
| 2,507,559 | * 5/1950 | D'Andrea | 15/220 |
| 2,634,444 | * 4/1953 | Coleman | 15/121 |
| 3,600,737 | 8/1971 | Shore | 15/104 |
| 3,731,337 | 5/1973 | Doyel | 15/220 |
| 3,751,750 | 8/1973 | Kaftan | 15/220 A |
| 3,759,621 | 9/1973 | De Carlo | 401/10 |
| 3,839,085 | 10/1974 | Hulvey et al. | 134/8 |
| 3,922,747 | 12/1975 | Kaftan | 15/220 |
| 3,933,407 | * 1/1976 | Tu et al. | 350/61 |
| 3,983,591 | 10/1976 | Ohtaki et al. | 15/28 |
| 4,144,091 | 3/1979 | Tran | 134/6 |
| 4,921,614 | 5/1990 | Frickman et al. | 210/695 |
| 4,977,637 | 12/1990 | Demers | 15/104 R |
| 5,515,570 | 5/1996 | Muscroft | 15/220.2 |
| 5,900,373 | 5/1999 | Otto-Nagels | 435/379 |

* cited by examiner

Primary Examiner—Sharidan Carrillo

(57) ABSTRACT

A diving mask fog wiping device and method which allows fog on the inside of the viewing face plate to be wiped by a slave unit which is magnetically coupled to a master unit on the opposite side of said viewing face plate. Further, the slave unit is magnetically coupled to a resting unit which keeps it out of the line of sight and near the surface of the viewing face plate while it is not being used for wiping. A porous and nonabrasive surface on the slave unit may be soaked in an antifog agent, allowing the agent to be applied and re-applied every time fog is wiped.

4 Claims, 1 Drawing Sheet

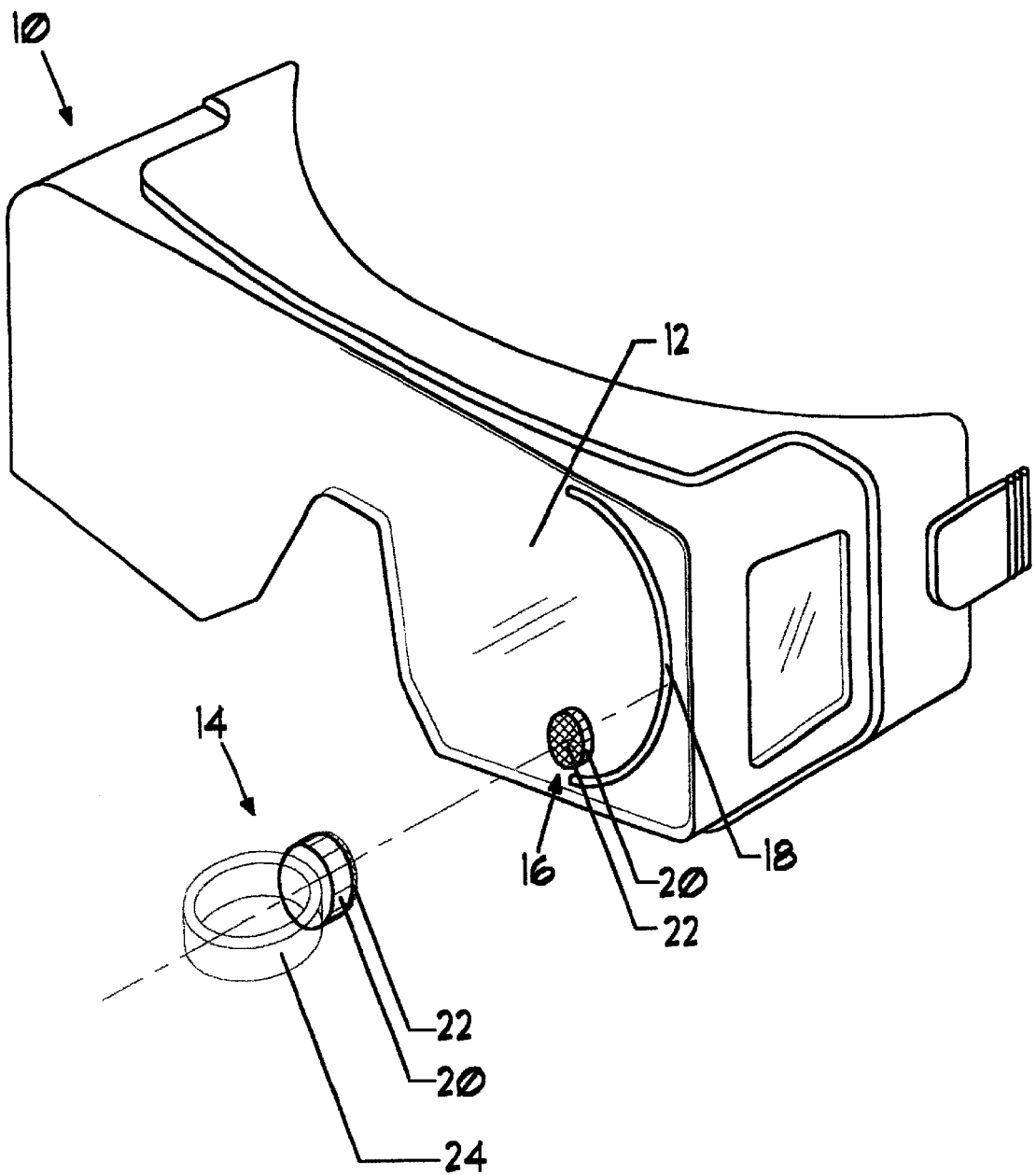

MAGNETIC APPARATUS AND METHOD FOR WIPING FOG IN A DIVING MASK

CROSS REFERENCE TO RELATED APPLICATIONS

Not applicable.

STATEMENT REGARDING FEDERALLY SPONSORED RESEARCH AND DEVELOPMENT

Not applicable.

BACKGROUND OF THE INVENTION

1. Field of Invention

This invention relates to diving, swimming, or other face masks, specifically to the wiping of fog from the inner surface of the viewing face plate(s).

Diving masks or swimming goggles are prone to the formation of fog on the interior surface of the viewing face plate(s). This occurs because of the moisture and temperature difference between the two sides of the glass. This fog (or more technically, condensation) is a significant viewing obstruction.

There exist diving masks equipped with so-called antifog lenses. However, these lenses appear only in the highest levels of professional equipment, and are not used in amateur-level equipment. As a result, most diving masks continue to fog-up.

There also exist methods and structures for defogging eye wear. Such methods and devices employ electrically generated heat or ventilation channels which are difficult to accommodate under water. For these reasons defogging methods and devices have not found their way into diving masks.

Currently, there exist only two methods for addressing the fog problem in diving masks: rinsing the fog via partial removal of the mask under water, and application of defogging agents to the interior side of the glass prior to the placement of the mask on the face. The first method has numerous disadvantages, including the call for considerable training, and loss of valuable air. The second method relies on the persistence of the defogging agent to remain on the glass, the impossibility of re-application under water, and health concerns over the use of chemicals.

A solution to all of these disadvantages is to provide a means of mechanically removing or wiping the fog without removing the mask, which is the function of our invention. In addition to several other components, our invention involves a pair of magnetically coupled units sandwiching the viewing face plate of the mask. Both units have at least one surface that is porous and nonabrassive, and one or both units are magnet, and if one is not a magnet, then it is magnetizable. In this way, the two units can be placed on either side of the glass—one on the inside (called the slave unit) and the other on the outside (called the master unit)—while magnetically coupled to one another. Then, any time the master unit is moved across the outside surface of the glass the slave unit follows in unison, thereby wiping fog off the inside surface of the glass. Furthermore, our invention involves a resting unit that provides a resting place for the slave unit while it is not being used.

2. Description of the Prior Art

U.S. Pat. Nos. 3,600,737, 3,731,337, 3,759,621, 3,839,085, 3,922,747, 3,983,591, 4,921,614, 4,977,637, and 5,515,570, are believed good examples of the state-of-the-art. All of these patents involve the magnetic coupling of two units disposed on the opposite sides of a surface.

Improvements on these patents have been made by addressing the status of the slave unit when it is not being used. U.S. Pat. No. 3,751,750 describes a "locator" for temporarily attaching to the window opposite the slave unit. U.S. Pat. No. 4,144,091 describes a "container" affixed to the slave-side of the window pane used for storing the slave unit. U.S. Pat. No. 5,900,374 describes a "holder" consisting of a pair of elastic wings which are adjusted at such an angle to hold the slave unit in place when it is not being used.

Such a "locator" requires access to both sides of the glass during operation; however, there is no access to the inside of a diving mask during operation and so, such a locator cannot be used. Since a diver wearing a mask moves his/her head from side to side and from up to down, a "container" cannot contain the slave unit, and if the slave unit exits the container, it not only can hit the divers face, but also leave the magnetic field region of the master unit and be lost in the mask. A "holder" has three disadvantages: 1) adjusting the angle and the elasticity of the wings is difficult, at best; 2) it can fail when there are wide variations in temperature and humidity in the medium wherein the device operates, as in under sea water, and 3) it has many moving parts, and so, can fail to capture the slave unit altogether.

Therefore, when the slave unit is not being used for wiping, it is crucial to assure that the slave unit is 1) removably affixed to the inside of the mask, so that when the master unit is brought to the outside of the glass the two can couple together, 2) rests sufficiently close to the inside surface of the glass, again, to allow magnetic coupling with the master unit when the latter is brought to the outside of the glass, and 3) kept out of the line of sight, and in a fail-safe fashion.

The primary difference between the current invention and all the prior art inventions is in having a resting unit, magnetically coupled to the slave unit when it is not being used. As such, it is simple to construct, without sensitive adjustments, insensitive to environmental conditions, and keeps the slave unit close to the viewing face plate and out of the line of sight. Without such a resting unit, none of the prior arts can be adapted to perform the function of wiping fog from the inside surface of the viewing face plate in a diving mask. Further, the resting unit can be simply trimmed and shaped to fit any mask, because it is a flexible, springy, wire (generally known as "piano wire" among hobbyists and model airplane builders).

It is important to emphasize that currently there does not exist any device for that purpose. What does exist is methods for rinsing the fog, means for avoiding fog, and methods that can be adapted to wiping fog. Our invention has numerous advantages over these alternatives, including the following: It 1) can be used continually and whenever desired, 2) is undepletable, 3) is chemical-free, 4) has no components that may wear out, and 4) has no sensitive moving parts, and so, cannot fail. Furthermore, if desired, defogging agents can be naturally incorporated into our invention by soaking the porous nonabrassive material on the slave unit in a defogging liquid, thereby allowing the defogging agent to be automatically applied and re-applied to the inside surface of the viewing face plate each time the device is used for wiping the fog.

BRIEF SUMMARY OF THE INVENTION

In accordance with the present invention, the diving mask or swimming goggle fog wiper consists of three magnetically interacting units called the master unit, the slave unit, and the resting unit. Both the master and the slave unit have at least one porous/nonabrasive surface. The master unit is on the outside of the mask, the slave unit is on the inside of the mask contiguous with the viewing face plate, and the resting unit is clamped to the inside of the mask also contiguous to the viewing face plate. When the device is not in use, the slave unit is magnetically coupled to the resting unit, thereby removably secured to the mask, kept close to the viewing face plate, and kept out of the line of sight. When the master unit is swept across the outside of the viewing face plate, due to its overwhelming magnetic attraction with the slave unit, the slave unit is detached from the resting unit and follows the motion in unison, thereby wiping fog off the inside of the viewing face plate. When the fog is wiped, the master unit is moved towards the resting unit at which point the slave unit is again magnetically coupled with the resting unit, ready to be used again.

Accordingly, the object of our invention is to provide means for wiping fog from the inside of a diving mask viewing face plate. Further objects and advantages are to provide a wiping means that fits diving masks and swimming goggles of any shape or size, is simple to install, has replaceable components, and is durable, lasting for a number of years. Another advantage of our invention is that it allows to delay the formation of fog by soaking the porous nonabrasive material of the slave unit in an antifog liquid. Still further objects and advantages will become apparent from a consideration of the ensuing description and drawings.

BRIEF DESCRIPTION OF THE DRAWING

The single FIGURE is a fragmentary view of a diving mask and the invention.

DETAILED DESCRIPTION OF THE INVENTION

The drawing shows a diving mask 10, its viewing face plate 12, a master unit 14, a slave unit 16, and the resting unit 18 that provides a resting place on which the slave unit can remain while device is not in use. The master unit is outside the mask and may be worn as a finger ring, or simply left on the outside of the viewing face plate, held in place due to its magnetic attraction with the slave unit or the resting unit. The master unit consists of a cylindrical magnet 20 with porous/nonabrasive material 22 on a side, and an adjustable ring 24. The magnet is attached to the nonabrasive surface and the adjustable ring by means of a water-proof adhesive. The slave unit 16 is inside the mask, and when not in use it is magnetically coupled to the resting unit 18; it is mostly identical to the master unit 14 except that it does not have a finger ring 24, or any other gripping means. The porous nonabrasive material 22 on the slave unit is spongy, thereby allowing it to absorb and maintain some amount of defogging liquid, if desired. The resting unit 18 consists of a clamp wire clamped inside the mask under tension with the walls of the mask; it is a magnetic or magnetizable, flexible, and springy wire that can be shaped to any desired shape. This FIGURE illustrates only the preferred embodiment of our invention; other embodiments are outlined below.

The relative strength of the magnetic interaction between the three units—the master, slave, and resting units—must be approximately specified. It is well-known to physicist and engineers that three such magnetically interacting objects constitute a problem that does not lend itself to analytic techniques of standard electromagnetism. As such only experimentation can provide a solution to the problem of finding the relative strengths of the fields between the three objects. The results of our experiments imply that an optimal design is provided if the magnets 20 of the master unit 14 and slave unit 16 are Neodymium magnets with a strength of 11,400 Gauss; the holding force of the master unit 14 magnet must be in the range of 0.8 to 0.9 Newtons (5.7 to 6.5 pounds), and that of the slave unit 16 must be in the range of 0.14 to 0.17 Newtons (1.0 to 1.2 pounds). With these holding forces it is not necessary for the resting unit 18 to be a magnet; a magnetizable material (with dimensions given below) will suffice.

Neodymium magnets are the strongest magnets that have been constructed, and as a result the size of the units can be kept sufficiently small as to not obstruct the view. In particular, both the master unit magnet 20 and the slave unit magnet 20 are cylindrical in shape, resembling small buttons, with a diameter in the range 9–13 mm (0.375–0.50 inches) and a thickness in the range 2–6 mm (0.1–0.25 inches). The optimal design calls for a resting unit 18 that is a magnetizable material such as a stainless steel wire of thickness 1–2 mm (0.05–0.1 inches). The length of the wire is determined by the shape of the mask 10. For masks with two separate viewing face plates 12, we find the optimal length of approximately 10 cm (4 inches) formed into a semi-circular ring with a radius of approximately 2.5 cm (1 inch). This provides a C-shaped frame that can be clamped into all such masks. For masks with a single viewing face plate 12, a single wire of approximate length 30 cm (12 inches) is found to provide sufficient perimeter upon which one or more the slave units 16 can find a resting place. As for the shape of this single wire, it can be trimmed and shaped to fit any diving mask.

The alternative embodiments of our invention include the following variations: The master unit 14 may be worn in numerous ways; it may be worn as a finger ring, attached to a finger-tip region of a glove, loosely attached to the diver or his/her equipment via a string or a Velcro strap, or even simply left on the outside of the viewing face plate, kept in place due its magnetic coupling with the slave unit 16 or the resting unit 18. The adjustable ring 24 may be in various fixed sizes, elastic, or velcro, thereby accommodating different finger sizes. The resting unit 18 may be a flexible wire covered by an elastic tube or coating rendering it nonabrasive and assuring a more firm disposal in the mask, or a magnetizable disc or strip adhered to the inside of the mask 10 close to or on the inner surface of the viewing face plate 12. The porous/nonabrasive material 22 on the salve unit 16 may be spongy so as to be soaked in a defogging agent, allowing for a longer lasting reservoir of the agent during the dive.

OPERATION

The operation of our invention calls for a one-step installation prior to placing the mask on the face. The installation consists of simply clamping the resting unit 18 to the inside of the mask near the inner surface of the viewing face plate 12, and placing a slave unit 16 against it. At this stage the device is ready for use.

To operate our invention under water the diver simply slides the master unit 14 across the outer surface of the viewing face plate 12, thereby causing the slave unit 16 to wipe the fog off the interior of the viewing face plate 12. When fog is wiped, the master unit 14 is moved to the vicinity of the resting unit 18, as a result of which the slave unit 16 is magnetically attracted back to the resting unit 18.

The operation of the alternative embodiments is identical to that of the main embodiment. The master unit 14 is moved across the outer surface of the viewing face plate 12, causing the slave unit 16 to detach from the resting unit 18 and follow the motion of the master unit 14, thereby wiping off the fog from the inner surface of the viewing face plate 12.

Therefore, it is evident that the magnetic wiper of our invention can wipe off fog from the interior of the viewing face plate 12, without removing the mask 10 from the face, and without the necessary use of chemical defoggers. If desired, antifog agents can be incorporated into our invention by soaking the porous/nonabrasive material 22 of the slave unit 16 in an antifog liquid allowing for the antifog agent to be re-applied every time fog is wiped, thereby delaying the formation of fog. Furthermore, our invention allows the wiping of the fog at any time, as many times, and as frequently as the diver wishes, without the need to remove the mask from the face, and without being limited by the active life time of a defogging agent.

Although the description above contains many specificities, these should not be construed as limiting the scope of the invention but as merely providing illustrations of some of the presently preferred embodiments of this invention. For example, one or both of the master and the slave units may contain a magnet, and of different shapes such as circular, square, etc. The resting unit may be of a different shape and material. There may be a flexible, elastic string segment securing the slave unit to the resting unit. The means of rendering all three units nonabrasive may be different. The method by which the master unit is attached to the user's hand, finger, other body part or equipment, may be different. Thus the scope of the invention should be determined by the appended claims and their legal equivalents, rather than by the examples given.

We claim:

1. A method of wiping fog from the inner surface of a face plate of a diving mask, comprising the steps of:
   a) providing a diving mask having a viewing face plate, said face plate having an inner and an outer surface;
   b) providing a movable magnetized master unit, said master unit comprising a first cylindrical magnet having a first porous nonabrasive material, wherein said master unit is positioned on the outer surface of the viewing face plate;
   c) providing a magnetized slave wiping unit, said slave wiping unit comprising a second cylindrical magnet having a second porous nonabrasive material, wherein said slave wiping unit is positioned on the inner surface of the viewing face plate;
   d) providing a magnetic spring wire resting unit for the slave wiping unit, said spring wire resting unit being located within the diving mask and adjacent the inner surface of the viewing face plate so as to be laterally out of the line of site of the diver, wherein the spring wire resting unit magnetically attracts and holds the slave wiping unit in place when said slave wiping unit is not in use;
   e) magnetically coupling said slave wiping unit to said magnetic spring wire resting unit;
   f) removing said slave wiping unit from said magnetic spring wire resting unit by magnetically coupling said master unit to said slave wiping unit; and
   g) moving said master unit across the outer surface of the face plate thereby causing said slave wiping unit to move across the inner surface of the face plate such that said slave wiping unit wipes off fog present on said inner surface of said face plate of the diving mask.

2. The method of claim 1, further comprising magnetically recoupling said slave wiping unit to said magnetic spring wire resting unit after wiping off fog from said inner surface of said face plate.

3. The method of claim 1, further comprising the steps of soaking said second porous nonabrasive material of said slave wiping unit with an antifog agent, and applying said antifog agent to said inner surface of said face plate every time fog is wiped off from the inner surface of the face plate.

4. A diving mask for removing fog comprising:
   a) a viewing face plate having an inner and an outer surface; and
   b) a fog wiping device comprising:
      a magnetized slave wiping unit, said slave wiping unit comprising a first cylindrical magnet having a first porous nonabrasive material, wherein said slave wiping unit is positioned on the inner surface of the viewing face plate;
      a magnetic spring wire resting unit for the slave wiping unit, said spring wire resting unit being located within the diving mask and adjacent the inner surface of the viewing face plate so as to be laterally out of the line of site of the diver, wherein the spring wire resting unit magnetically attracts and holds the slave wiping unit in place when said slave wiping unit is not in use; and
      a manually movable magnetized master unit positioned on the outer surface of the viewing face plate, said master unit comprising a second cylindrical magnet having a second porous nonabrasive material, wherein said master unit magnetically couples to said slave wiping unit and moves said slave wiping unit across the inner surface of the face plate such that said slave wiping unit wipes off fog present on said inner surface of said face plate.

* * * * *